US008840588B2

(12) United States Patent
Clement et al.

(10) Patent No.: US 8,840,588 B2
(45) Date of Patent: Sep. 23, 2014

(54) INSUFFLATION NEEDLE WITH DUAL INDICATOR AND METHOD OF USE

(75) Inventors: Thomas P. Clement, Bloomington, IN (US); David P. Weber, Bloomington, IN (US)

(73) Assignee: Mectra Labs, Inc., Bloomfield, IN (US)

( * ) Notice: Subject to any disclaimer, the term of this patent is extended or adjusted under 35 U.S.C. 154(b) by 136 days.

(21) Appl. No.: 13/372,494

(22) Filed: Feb. 13, 2012

(65) Prior Publication Data

US 2012/0209167 A1     Aug. 16, 2012

Related U.S. Application Data

(60) Provisional application No. 61/441,934, filed on Feb. 11, 2011.

(51) Int. Cl.
| | | |
|---|---|---|
| *A61M 5/178* | (2006.01) | |
| *A61B 17/34* | (2006.01) | |
| *A61M 13/00* | (2006.01) | |
| *A61B 19/00* | (2006.01) | |
| *A61B 17/00* | (2006.01) | |

(52) U.S. Cl.
CPC ...... *A61M 13/003* (2013.01); *A61B 2019/4857* (2013.01); *A61B 2017/00115* (2013.01); *A61B 17/3474* (2013.01); *A61B 17/3496* (2013.01)
USPC ............. 604/170.01; 604/164.12; 604/164.01

(58) Field of Classification Search
USPC ............. 604/110–111, 506, 93.01, 116–117, 604/164.01, 164.12, 170.1, 171
See application file for complete search history.

(56) References Cited

U.S. PATENT DOCUMENTS

| | | |
|---|---|---|
| 4,379,458 A | 4/1983 | Bauer et al. |
| 4,535,773 A | 8/1985 | Yoon |
| 4,601,710 A | 7/1986 | Moll |
| 4,654,030 A | 3/1987 | Moll et al. |
| 4,808,168 A | 2/1989 | Warring |
| 4,869,717 A | 9/1989 | Adair |
| 4,902,280 A | 2/1990 | Lander |
| 4,931,042 A | 6/1990 | Holmes et al. |
| 5,098,388 A | 3/1992 | Kulkashi et al. |
| 5,139,485 A | 8/1992 | Smith et al. |
| 5,256,148 A | 10/1993 | Smith et al. |
| 5,290,276 A | 3/1994 | Sewell, Jr. |
| 5,338,083 A * | 8/1994 | Gute ............................ 296/97.9 |
| 5,366,445 A * | 11/1994 | Haber et al. ............. 604/164.01 |
| 5,383,859 A | 1/1995 | Sewell, Jr. |
| 5,423,796 A * | 6/1995 | Shikhman et al. ................ 606/1 |
| 5,429,636 A | 7/1995 | Shikhman et al. |
| 5,449,370 A | 9/1995 | Vaitekunas |
| 5,450,182 A | 9/1995 | Wayman et al. |

(Continued)

FOREIGN PATENT DOCUMENTS

WO     WO9739680 A1     10/1997

*Primary Examiner* — Nicholas Lucchesi
*Assistant Examiner* — Weng Lee
(74) *Attorney, Agent, or Firm* — Barnes & Thornburg LLP

(57) ABSTRACT

A medical apparatus which comprises a sharpened outer needle and a blunt inner needle slidingly disposed within the outer needle is provided. The apparatus also contains a position indicator to indicate the position of the inner needle within the outer needle, so that the user knows whether the inner needle is in a protective or a non-protective position. The position indicator may be a mechanical visual indicator, an electronic visual indicator, a tactile indicator, an audible indicator or any combination of the above.

18 Claims, 8 Drawing Sheets

(56) References Cited

U.S. PATENT DOCUMENTS

| | | |
|---|---|---|
| 5,460,182 A | 10/1995 | Goodman |
| 5,669,883 A | 9/1997 | Scarfone et al. |
| 5,797,906 A | 8/1998 | Rhum et al. |
| 5,853,392 A | 12/1998 | Dennis |
| 6,059,759 A | 5/2000 | Mottola et al. |
| 6,228,058 B1 | 5/2001 | Dennis et al. |
| 6,245,091 B1 | 6/2001 | Buncke |
| 6,447,483 B1 * | 9/2002 | Steube et al. .................. 604/158 |
| 7,329,233 B2 | 2/2008 | Gresham |
| 7,413,559 B2 | 8/2008 | Stubbs et al. |
| 2006/0265035 A1 | 11/2006 | Yachi et al. |
| 2008/0249467 A1 | 10/2008 | Burnett et al. |
| 2009/0234273 A1 | 9/2009 | Intocia et al. |

* cited by examiner

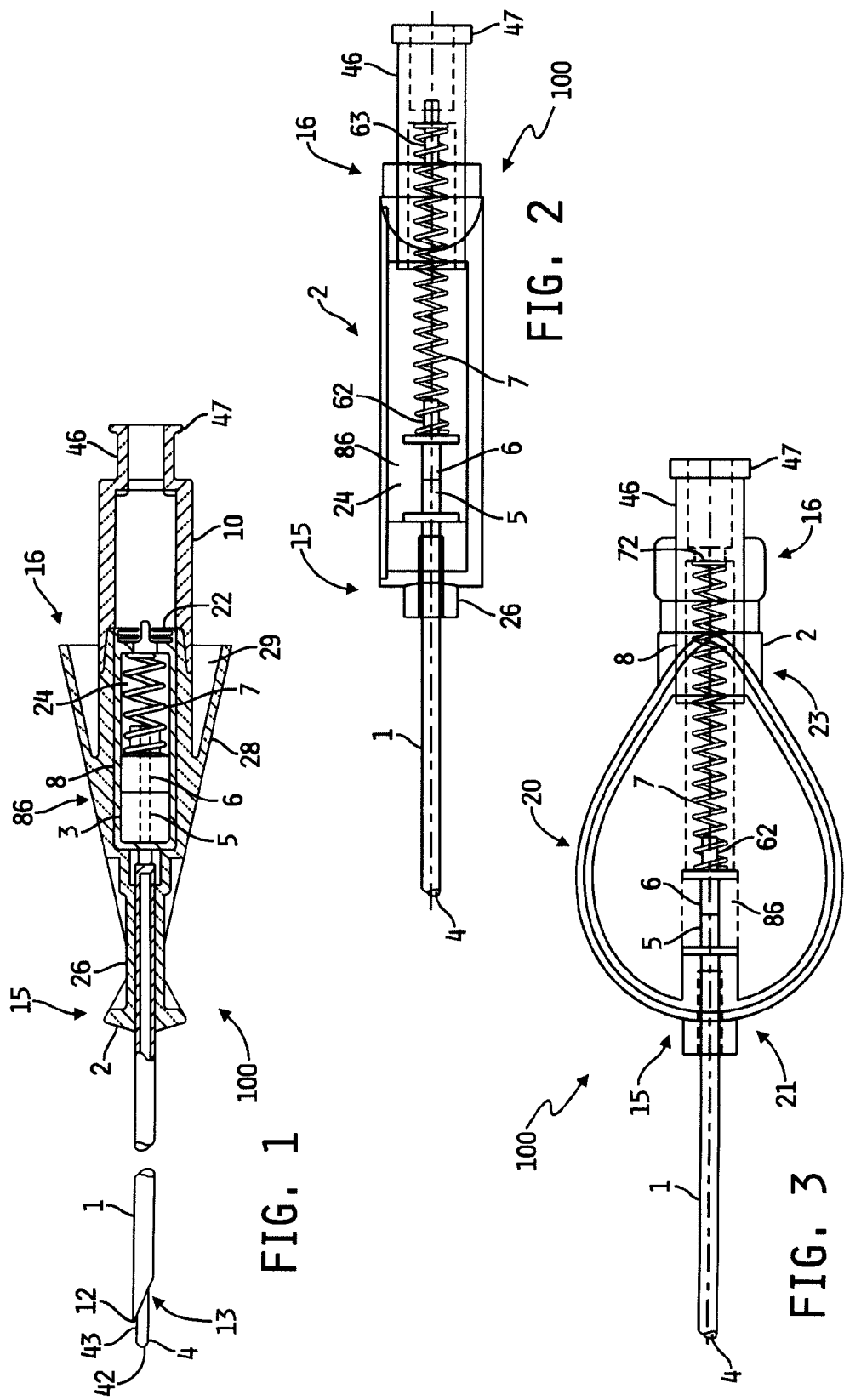

INSUFFLATION NEEDLE WITH DUAL INDICATOR AND METHOD OF USE

This application claims priority to and the benefit of U.S. Provisional Patent Application No. 61/441,934, filed 11 Feb. 2011, the disclosure of which is now incorporated by reference herein.

FIELD OF THE INVENTION

This invention relates generally to medical instruments. More particularly, the invention relates generally to an apparatus and method for safely puncturing body tissue, and more specifically to a surgical instrument having at least a single position indicator to positively indicate both when the puncturing portion is in a protective position and when it is in a non-protective position.

BACKGROUND OF THE INVENTION

In various medical procedures, one or more surgical instruments may be used to puncture or penetrate body tissue. The body tissue may be penetrated in order to insert the instrument into a body cavity such as for example the abdominal cavity. Throughout the present application, the terms penetrating, piercing and puncturing and formatives thereof are used interchangeably. For example an instrument known as a trocar that generally comprises a sharp pointed instrument, may be used to penetrate the abdominal wall to create an access hole therethrough into the abdominal cavity. In another example, an instrument known as a Veress needle or insufflation needle may be used. Veress-type needles use a hollow, blunt inner needle capable of fluid passage, and to carry insufflating gas into the abdominal cavity. A stopcock and valve assembly is connected to the inner needle. The inner needle and valve assemblies are pushed rearward by resistance on the needle end and are biased forward by a spring when the resistance is removed. Thus, Veress needles generally comprise a hollow outer needle having the end opposite the pointed end rigidly secured to a handle or a handle-like housing. A tube or hollow needle or stylet illustratively is slidably carried or disposed within the hollow needle. One end of the tube is typically secured to one end of a piston-like hollow plunger slidably retained within a plunger cylinder formed in the handle or handle-like housing. The other end of the plunger is typically attached to one end of a bias member such as for example a spring, the other end of which is connected to the top end of the plunger cylinder or other handle portion. A centrally located axially directed hole through the housing connects the interior of the plunger cylinder to a port at the end of the housing for receiving a stopcock, petcock or valve mechanism. The other end of the tube typically projects beyond the needle point, with the tube having a gas exit hole through the side of the tube proximate the tip. The tube is oriented within the needle to insure that the gas exit hole of the tube is not blocked by the needle when the tubing end is protruding from the needle via the spring biasing. The free or protruding end of the hollow tube is closed off, typically via a plug.

Needles to create pneumoperitoneum are used to insufflate the abdominal cavity to facilitate endoscopic examination and surgery. Laparoscopic surgical procedures require that a fluid or gas, such as carbon dioxide, be introduced into the abdominal cavity. This establishes pneumoperitoneum wherein the peritoneal cavity is sufficiently inflated for the insertion of trocars into the abdomen. The fluid may be introduced using a Veress or insufflation needle. A Veress-type pneumoneedle has a spring-loaded, blunt tipped inner needle contained within a larger diameter piercing needle. The larger diameter needle is hollow and allows for passage of the blunt needle therein. In using such a needle a physician or user illustratively pushes the free end of the tube against the body tissue, muscles and/or membranes forming the cavity wall of for example the abdomen of a patient. Once the Veress-type needle penetrates the abdominal wall, and enters the body cavity, the resistance against the end of the Veress-type needle is removed, so that the spring force causes the blunt needle or tube to move forward, to extend beyond the sharp tip of the outer needle. This allows the needle to enter the body without puncture or laceration of any abdominal structures. In other words, the tube retracts against the spring biasing, permitting the relatively sharper needle end to be forced for example through the abdominal wall into the abdominal cavity, whereafter the free end of the relatively blunt inner tube pops out or extends from the relatively sharp needle via the spring biasing, thereby exposing the gas exit hole or aperture. This, of course, assumes that the needle is in an open area of the illustrative abdominal cavity or other body cavity, and is not pushing against some other body tissue such as for example an internal organ or muscle, which would prevent the inner tube from so popping out or moving to its extended position relative to the needle. The physician can then connect a gas line to the valve or petcock, and cause gas to enter into the Veress needle, pass through the tube and exit out of the gas exit hole of the tube into the abdominal cavity for insufflating the abdominal cavity. Alternatively, fluid can either be forced into or sucked from the abdominal cavity or other body cavity through use of the Veress needle.

If the needle goes beyond the peritoneum, the needle may perforate the stomach, small bowel, colon, bladder, or major vascular structures, the consequences of which can be fatal. The purpose of the spring-loaded safety tip of the Veress needle is to minimize the risk of visceral injury by covering the sharp tip once it has penetrated the peritoneum and reached a void. Generally, the surgeon relies on tactile senses to determine the proper placement of the needle by recognizing when the needle is inserted through the fascia and then through the peritoneum. However, this technique is often unreliable. It is sometimes difficult for a user, physician or surgeon to ascertain when the internal cavity wall has been breached by the Veress needle or trocar. Typically, the only indication is a reduction in the amount of resistance felt by the surgeon, with perhaps a mechanical vibration or sound caused by the forward movement of the spring biased needle or stylet once the internal cavity has been breached. Various devices have been developed to provide a more positive indication of when the cavity wall has been breached. These devices typically utilize visual or audible signals.

Some relevant examples of Veress needle and trocar instruments include Bauer et al., U.S. Pat. No. 4,379,458; Yoon, U.S. Pat. No. 4,535,773; Moll, U.S. Pat. No. 4,601,710; Moll et al., U.S. Pat. No. 4,654,030; Warring, U.S. Pat. No. 4,808,168; Adair, U.S. Pat. No. 4,869,717; Lander, U.S. Pat. No. 4,902,280; and Holmes, U.S. Pat. No. 4,931,042; Kulkashi et al., U.S. Pat. No. 5,098,388; Sewell, Jr., U.S. Pat. No. 5,290,276; Smith et al., U.S. Pat. No. 5,256,148; Scarfone et al., U.S. Pat. No. 5,669,883; Dennis, U.S. Pat. No. 5,853,392; and Buncke et al., U.S. Pat. No. 6,245,091; the disclosures of all of which are now expressly incorporated herein by reference.

After establishing pneumoperitoneum, the next step in laparoscopic surgery involves the insertion of a trocar into the abdominal cavity. It is through this first trocar that an endoscope is inserted into the abdominal cavity to provide the surgeon with a view of the rest of the operation. Trocars are similar to the Veress needle in that they are also equipped with a spring-loaded safety shield to avoid visceral injury. Trocars, like Veress needles, are inserted using a sudden thrust of the pointed tip into the abdomen. Therefore, as is true with the Veress needle, placement of the trocar is also vital, and the reliance of the surgeon on mere tactile senses for proper placement can be fatal.

SUMMARY OF THE INVENTION

The present invention may comprise one or more of the features and combinations thereof set out below or in the claims appended hereto.

A medical apparatus is provided. Illustratively, the medical apparatus is configured for performing surgical procedures, such as for example and without limitation laparoscopic surgery. For example and without limitation, the medical apparatus may be configured to penetrate a body cavity and introduce or remove items from the body cavity. fluid. The medical apparatus illustratively may comprise a hollow outer tube, a hollow inner tube, a handle, and a position indication system.

The inner tube and the outer tube may be fashioned out of any suitable metallic, non-metallic or composite material, or any combination thereof, by any method of manufacture suitable to the material used. For example, the tube(s) could be made in whole or in part from titanium, platinum, silver, gold, brass, bronze, aluminum, lead, copper, chrome, vanadium, martensite chrome steel, steel, stainless steel, plastic, kevlar, poly-carbonate, and the like or any combination thereof. Illustratively, the inner tube and the outer tube comprise stainless steel. It will be appreciated that the tubes may comprise a trocar, a cannula and/or a needle, including for example and without limitation a Veress, Veress-type of insufflation needle. Each of the tubes, which illustratively are elongated, have a respective proximal end and a respective distal end. In one illustrative case, for example a Veress-type needle, the distal end of the inner tube illustratively may have a blunt tip, and illustratively may include one or more apertures or sufflation holes in the distal end in the vicinity of the blunt tip. The distal end of the outer tube illustrative may have a sharpened tip. Illustratively, the inner tube defines a hollow core extending from the inner tube's proximal end to the inner tube's distal end. Illustratively, the outer tube defines a hollow core extending generally from the outer tube's proximal end to the outer tube's distal end. The inner tube illustratively is disposed or received within the outer tube. The outer tube and the inner tube illustratively are in sliding relationship. More specifically, the inner tube illustratively slides within the outer tube. In the case of a trocar, the apparatus may be used to insert into the body cavity one or more other surgical instruments. In the case of an insufflation needle, the apparatus may be used to insert or remove fluid from the body cavity. For example and without limitation, the carbon dioxide may be introduced and removed from the body cavity through the medical apparatus. The distal end of the outer handle and the proximal end of the outer needle may be coupled or joined together. Illustratively, the outer needle and the handle are rigidly connected to one another.

The handle illustratively has a distal end and an operative end. The handle may be fashioned out of any suitable metallic, non-metallic or composite material, or any combination thereof, by any method of manufacture suitable to the material used. Illustratively, for example and without limitation, the handle may be molded from clear poly-carbonate. The handle defines an interior chamber or channel. Illustratively, the interior chamber may be generally elongated, having a rectangular profile in plan view. The handle illustratively may define a viewing window. The handle may also include a manipulation portion. The manipulation portion may take on various desired shapes. For example and without limitation, it may comprise a generally arcuate distal end proximate to the distal end of the handle and may tapir to a more pointed or triangular proximal end proximate to the operative end of the handle. The tapir may comprise a concave or a convex tapir between the distal and proximal ends of the manipulation portion. For example, the manipulation portion in plan view may resemble a face with an ovate distal end resembling the top of the face and cheeks, tapering down to the triangular operative end resembling a chin. The manipulation portion may include a cover or top face. The top face illustratively may define a plurality of apertures. The plurality of apertures may comprise one or more of the following, the above mentioned viewing window, a diode aperture, a power switch aperture, and an alternate aperture as will be explained. In the illustrative case of the manipulation portion resembling a face, two diode apertures having an elliptical or oblate shape could be spaced apart in the nature of eye sockets toward the distal end. Similarly, the power switch aperture could have a quadrilateral shape or other elongated shape, such as for example a rectangle, and be placed generally between the diode apertures, but more in the middle of the face. The alternative aperture could be generally arcuate, resembling a grinning mouth, and placed generally in the middle of the face, between the power switch aperture and the operative end of the manipulation portion. In another illustrative case, the manipulation portion could be formed to resemble a door key, with the distal end being arcuate as the bow of a key and tapering toward the operative end, which resembles the blade of a key. The top face of such an illustrative key shaped manipulation portion may also define or include one or more apertures, such as for example the viewing window. It will be appreciated that a user, for example a surgeon or other physician, could grasp the manipulation portion, for example in the vicinity of the tapir, and apply pressure thereto in order to apply the force necessary to puncture body tissue. The manipulation portion illustratively may serve as a housing for the position indication system.

The medical apparatus further comprises a bias means or a bias member, for example and without limitation a spring. Illustratively, the bias member is disposed in the interior chamber, sandwiched between the proximal end of the inner tube and the operative end of the handle. The spring normally exerts a force to urge, extend or express the inner tube or needle into a first position generally outwardly and away from the operative end.

The position indication system illustratively includes a first indicator and a second indicator that provide a perceivable indication or signal of the position of the inner needle or tube relative to the generally fixed outer needle or tube. Illustratively, the first indicator and the second indicator comprise a single integrated component. The first indicator illustratively comprises a positive indicator and the second indicator illustratively comprises a negative indicator. For example and without limitation, the first indicator informs a user that one or the other of the tubes, for example, the inner tube is in the normal first position. Illustratively, the first position is a safe position. The second indicator illustratively informs a user that the inner tube is in a second or unsafe position. Illustratively, the first or safe position is where the blunt or dull tip extends beyond the sharp tip. When the inner tube is in this safe position, the positive indicator is perceptible by a user and the negative indicator is not perceptible. The inner tube illustratively moves to the second, retracted or unsafe position when a force sufficient to overcome the normal extending or expressing force of the bias member is applied to the blunt tip, thereby moving the hollow inner tube inwardly toward the operative end such that the blunt or dull tip no longer extends beyond the sharp tip. In the unsafe position, illustratively, the negative indicator is perceptible by a user and the positive indicator is not perceptible by a user. It will be appreciated that the position indication system may comprise different perceptible means. For example and without limitation it may comprise a visible indication system, an audible or aural indication system, a tactile indication system, or any combination of the foregoing. For example the position indication system may comprise a combination of a visible indication system and a tactile indication system, may comprise a combination of a visible indication system and an audible indication system, may comprise a combination of an audible indication system and a tactile indication system, and may comprise a combination of a visible indication system, a tactile indication system, and an audible indication system. So, too, the visual indication system may comprise a mechanical indication system, an electronic indication system, a chemical indication system, an infra-red indication system, a visible light indication system, a radio frequency indication system or any combination of the foregoing, for example and without limitation an electro-mechanical indication system. Of course, the position indication system may comprise a plurality of any of the foregoing systems. For example, there may be more than one type of visual indication system, alone or in combination with one or more of the other types of indication systems.

Illustratively, the mechanical visual indication system comprises a two-colored indicator. The two-colored indicator is integral such that a single unit provides both the first indicator and the second indicator. More specifically, the integrated indicator displays for a user a first color when the inner needle is in the safe position and a second color when the inner needle is in the unsafe position. When the first color is perceptible by a user, the second color is not perceptible by a user. Conversely, when the second color is perceptible by a user, the first color is not perceptible by the user. In one illustrative embodiment, the integral two-colored indicator may comprise a two-colored bobbin. In another illustrative embodiment, it may comprise a spring clip or position indicating member having a generally planar portion or array that exhibits two colors. For example, the planar array may have an upper portion and a lower portion. The upper portion may comprise the color of the first color, and the lower portion may comprise the color of the second color. Whether a bobbin or a spring clip having a planar array, or some other type of integral two-colored indicator, the two-colored indicator and the inner tube may be coupled together. Thus, the planar array and the inner tube illustratively move together in unison within the interior chamber. The viewing window illustratively is defined by the handle, or a cover having a top face coupled to the handle. The viewing window may comprise a magnifying lens. The viewing window may be configured on the handle such that when the inner tube is in the safe position, the first color of the upper portion and the viewing window are aligned thus allowing the first color to be perceived and the second color to be masked by for example the top face of the cover or handle. Conversely, when the inner tube is in the unsafe position, the second color of the lower portion and the viewing window are aligned, thus allowing the second color to be perceived and the first color to be masked.

In another illustrative example, an electrical or electronic visual indication system illustratively comprises a light emitting diode (LED) configured to emit at least two distinct signals, illustratively two colors. It will be appreciated that other sources capable of producing two distinct signals may be used. For example and without limitation, fiber optics, gas tubes, radiation tubes, chemical tubes, and the like and signals produced by chemoluminescence, phosphorescence, and fluorescence and the like may be used. Illustratively, the LED is capable of displaying or emitting the first color and the second color. The LED emits the first color, and the first color only, when the inner tube is in the safe position. Conversely, the LED emits the second color, and the second color only, when the inner tube is in the unsafe position. Thus, a user can perceive the first color only when the inner tube is in the safe position and perceive the second color only when the inner tube is in the unsafe position. The Illustratively, the electrical or electronic visual indication system further comprises a second LED, which can also emit at least two colors and which operates exactly as just described for the first LED. The electrical visual indication system further comprises a circuit board having a first color contact and a second color contact. It also comprises a slide contact and a power source. The power source may be any AC or DC electrical power source. For example the system could be provided with a power cord for plugging into an electrical outlet. Illustratively the power supply is a battery. The battery may be disposed within the handle, but illustratively is carried by the circuit board, which is disposed within the handle or manipulation portion. A power switch is also carried by the circuit board, and is slidingly disposed to move between a first position and a second position. In the first position, the electrical or electronic visual indication system is deenergized, and in the second position the electrical or electronic visual indication system is energized by the power source. Similar to the two-colored mechanical array, the slide contact is coupled together with the inner tube. Thus, the slide contact and the inner tube move together in unison within the handle such that when the inner tube is in the safe position, the slide contact and the first color contact are in electrical contact with each other and the LED(s) emit the first color, but not the second color. When the inner tube is in the unsafe position, the slide contact and the second color contact are in electrical contact with each other and the LED(s) emit the second color, but the slide contact and the first color contact are no longer in electrical contact with each other such that the first color is no longer emitted. Illustratively, the LED(s) may be disposed within or protrude from the LED apertures in the top face, and the power switch may be disposed within or protrude from the power switch aperture in the top face. The power switch may move within the power switch aperture. In addition, the power switch could be disposed and move within the alternate aperture if desired. In any event, illustratively, the LED(s) would resemble eyes in eye sockets and the power switch would resemble a nose, and the alternate aperture resembles a mouth on the face.

Illustratively, each of the first and second colors may be any of color in the visible light spectrum, color palette, color wheel, or color space chromaticity diagram. For example and without limitation any shades of red, orange yellow, green, blue, brown, black, indigo, violet, white, cyan, and magenta may be used. It will be appreciated that colors in the non-visible range could also be used. For example, if the user were using a viewing device operating in the infrared or ultraviolet spectrum, then the first and second colors could be chosen in that spectrum. Illustratively, the first color comprises green and the second color comprises red. Illustratively green signifies to user a positive indication such associated with green such as "go" or "gas."

Illustratively, the tactile indication system comprises a vibration generation system. The vibration generation system illustratively causes the apparatus to vibrate when the inner needle is in the unsafe position, and to cease vibrating when the inner needle is in the safe position. If desired, however, the vibration generation system could be configured to cause the apparatus to vibrate when the inner needle is in the safe position, and to cease vibrating when the inner needle is in the unsafe position. Similar to the LED system, the vibration generation system could comprise a power supply and contacts that move in unison with the inner needle in order to complete or open an electronic circuit to enable or disable vibration as desired.

Illustratively, the audible indication system emits an audible signal when the inner needle is in the safe position, and wherein the audible indication system ceases to emit an audible signal when the inner needle is in the unsafe position or vice versa. In addition, the audible indication system could emit a first audible signal when the inner needle is in the safe position and a second audible signal when the inner needle is in the unsafe position. The audible signal may be mechanical, as when the bias member urges or expresses the inner needle forward, or it may be electrical. For example, it could comprise a power supply and contacts that move in unison with the inner needle in order to complete or open an electronic circuit to emit the audible signal or signals as desired The handle may further comprise a fluid tube extension, which may include a shoulder, flange, waist, or ridge. The flange or waist may be configured to connect with a stopcock, pet cock or valve. For example, a threaded valve or stop cock may screw on over the flange. The valve may be in fluid communication with a fluid source, for example a carbon dioxide supply. The fluid tube, the handle chamber, and the inner tube may all be in fluid communication with one another. In operation, opening the valve illustratively allows fluid to flow through the fluid tube, through the handle, through the inner tube and out through the sufflation hole or aperture.

Also provided is an illustrative medical apparatus comprising: a hollow outer tube having a proximal end and a distal end, the distal end being sharpened; an inner tube or needle having a proximal end and a distal end, the distal end being blunt or dull, and the inner tube defining a hollow core extending from the inner tube's proximal end to the inner tube's distal end, the distal end including an aperture in fluid communication with the hollow core; a handle having a distal end and an operative end and defining an interior chamber, and including a viewing window; an integral dual-position indicator system having a positive indicator and a negative indicator; and a bias member having a distal end and a proximate end; wherein the proximal end of the outer tube and the distal end of the handle are connected together; wherein the hollow inner tube is slidingly disposed within the hollow outer tube and the interior chamber, with the proximate end of the inner tube being coupled with distal end of the bias member, and the proximate end of the bias member and the operative end of the handle being in contact with one another; wherein the position indicator system is coupled together with the inner tube and disposed on the outside of a portion of the inner tube that is disposed within the chamber, adjacent to the viewing window; and wherein the bias member normally urges the inner hollow tube outwardly away from the operative end to a first position wherein the blunt or dull tip extends beyond the sharp tip thereby moving the positive indicator into alignment with the viewing window so that the positive indicator alone is visible by a user of the apparatus; and wherein when a force sufficient to overcome the normal force of the bias member is applied to the blunt end the positive indicator, the inner hollow tube moves to a second retracted position wherein the blunt or dull tip no longer extends beyond the sharp tip thereby removing the positive indicator from alignment with the viewing window and moving the negative indicator into alignment with the viewing window so that the negative indicator alone is visible by a user.

Also provided is an illustrative Veress-needle comprising: a handle having proximal and distal ends connected to a hollow outer needle with an end portion for penetrating a body cavity, said hollow outer needle and said handle providing a conduit through which fluid may be passed to or from the body cavity, said hollow outer needle attached to said handle at the distal end of said handle; a hollow inner needle having proximal and distal ends surrounding an elongated body, which extends through said hollow outer needle and into said conduit in said handle, said inner needle having an opening near its distal end, and an open portion at its proximal end within said handle; a spring housed within said conduit of said handle at said proximal end of said handle and said inner needle for biasing said inner needle forwardly to a protective position, so that the distal end of said inner needle extends past the end portion of said outer needle absent resistance against said inner needle; and dual indication means contained on said handle for informing a user when the inner needle is moved to its protective position and when it is moved out of its protective position.

An illustrative insufflation needle is provided. The insufflation needle illustratively comprises: a hollow outer needle with a sharp distal end, a handle coupled to the proximal end of the outer needle, and a spring biased blunt tipped inner stylet which extends through the outer hollow needle. The inner blunt tipped stylet is normally biased to a first position which extends beyond the sharp distal end of the hollow outer needle and is movable against its biasing spring into the hollow outer needle. An integrated, dual indicator in the handle illustratively indicates the position of the inner stylet relative to the outer needle. A distal portion of the handle is tapered and has a groove or waist which is arranged to receive and retain a luer lock coupler. A rotatable luer lock coupler may be snap-fit onto the waist of the handle.

Another illustrative medical apparatus comprises means for puncturing a body cavity, means for passing fluid to or from the body cavity, and means for indicating when the means for puncturing is enabled and when the means for passing fluid is enabled. The means for puncturing a body cavity may comprise for example and without limitation a trocar or an elongated hollow tube having a sharp end. The means for passing fluid may comprise for example and without limitation an elongated hollow tube having a blunt end. The blunt ended tube may be slidingly disposed within the sharp-ended hollow tube and may illustratively comprise an insufflation needle. The means for indicating may comprise a dual-position indication system. The indication system may comprise a mechanical visual indication system, an electrical or electronic visual indication system, an aural indication system, a tactile indication system, or any combination of one or more of the foregoing.

Further provided is a method of performing a medical procedure comprising the steps of: providing a puncturing apparatus comprising nested hollow tubes in sliding relationship to one another; urging one of the nested tubes to an extended position wherein a distal end of the one nested tube extends beyond a distal end of the other nested tube; and providing an indication system that provides a first indication when the one nested tube is in the first position and a second indication when the one nested tube is moved to an unextended position wherein the distal end of the one nested tube does not extend beyond the distal end of the other nested tube.

These and other aspects of the invention are accomplished in a Veress-type pneumoneedle which contains a hollow outer needle or tube with a sharpened point, allowing passage of a spring-biased blunt tipped inner needle or tube. This hollow outer needle is placed on a handle. Contained within the handle is an indicator system such as for example a circuit board, which generates a visual signal to indicate that the blunt tipped inner needle or tube has been expressed forward, so that its blunt end extends beyond the sharp tip of the outer needle, and a different signal to indicate that the blunt tipped inner needle has been retracted, so that the sharp outer tip is exposed.

Additionally, the surgical instrument may be made sensitive to passage of the point of a penetration implement through an organ structure and fitted with a switch for triggering a sensible signal to alert a surgeon when the point has punctured the cavity wall. Accordingly, it is desirable to provide an indication system in order to determine whether the blunt tip of the inner needle or tube has been expressed forward past the sharpened end of the hollow needle or tube. The signal may be tactile, aural, or visual.

It is yet another aspect of the invention to provide indication means to determine both that the blunt tip of the needle has been expressed or moved forward, past the hollow sharpened outer needle, and has been retracted to expose the sharpened outer needle. It is a further object to provide a device to supply a signal when a sharp point of a surgical instrument successfully penetrates an anatomical cavity. Yet another aspect of the invention is to provide a Veress needle assembly with a dual visual indicator that the pointed end of the needle is either against the abdomen outer wall, preparatory to penetrating the abdominal wall, or that thereafter the point of the needle is against some interior body member within the abdominal cavity, thereby minimizing injury to internal organs. Further, the handle may contain a lens-magnified color indicator, to indicate the location of the blunt tipped needle. This feature comprises two colored bands. The two colored bands are integrated in a single visual indicator. The color bands may be magnified by a lens. One of the colored bands indicates that the blunt end of the inner needle is moved forward and extends beyond the sharp tip of the outer needle. The opposite colored band indicates that the blunt end of the inner needle has not yet been moved forward. This visual signal helps prevent punctures and lacerations of the abdominal cavity by the sharpened tip of the outer needle.

Also provided is a medical apparatus comprising a hollow outer tube having a proximal end and a distal end, the distal end comprising a sharpened tip; an hollow inner tube having a proximal end and a distal end, the distal end comprising a blunt tip, and the inner tube defining a hollow core extending from the inner tube's proximal end to the inner tube's distal end, the distal end including an aperture in fluid communication with the hollow core; a handle having a distal end and an operative end and defining an interior chamber; a position indicator system having a first indicator and a second indicator; a bias member having a distal end and a proximal end; wherein the proximal end of the outer tube and the distal end of the handle are connected together; wherein the hollow inner tube is slidingly disposed within the hollow outer tube and the interior chamber; wherein the distal end of the bias member extends inwardly through an aperture in the proximity of the proximal end of the hollow inner tube to couple together the hollow inner tube and the bias member; wherein the position indicator system includes an indicating assembly (for example an indicating window or a transducer, or a vibrator, or LEDs, or an IR receiver, etc.) and a position indicating (for example a spring clip) carried by the hollow inner tube; wherein the position indicating member includes a bend having a first aperture on one side of the bend and a second aperture on another side of the bend, the first and second apertures being opposed to and in alignment with one another and wherein the hollow inner tube extends through the first and second opposed apertures on either side of the bend; wherein the position indicating member is disposed within the chamber and operatively associated with the position indicating member; wherein the bias member normally urges the hollow inner tube outwardly away from the operative end to a first position wherein the blunt tip extends beyond the sharpened tip thereby moving the position indicating member into operative alignment with a portion of the indicating assembly that enables the first indicator alone; and wherein when a force sufficient to overcome the normal force of the bias member is applied to the blunt end the hollow inner tube, the hollow inner tube moves to a second retracted position wherein the blunt tip no longer extends beyond the sharpened tip thereby removing the position indicating member out of operative alignment with the portion of the indicating assembly that enables the first indicator alone and into operative alignment with a second portion of the indicating assembly that enables the second indicator alone.

These and other aspects and features of the present invention will become more apparent from the following description of the illustrative embodiment.

BRIEF DESCRIPTION OF THE DRAWING

FIG. 1 is a cross-sectional view of an illustrative needle;

FIG. 2 is a cross-sectional view of another illustrative needle;

FIG. 3 is a top partial cross-sectional plan view of another illustrative needle;

DESCRIPTION OF THE ILLUSTRATIVE EMBODIMENTS

Figure 4:
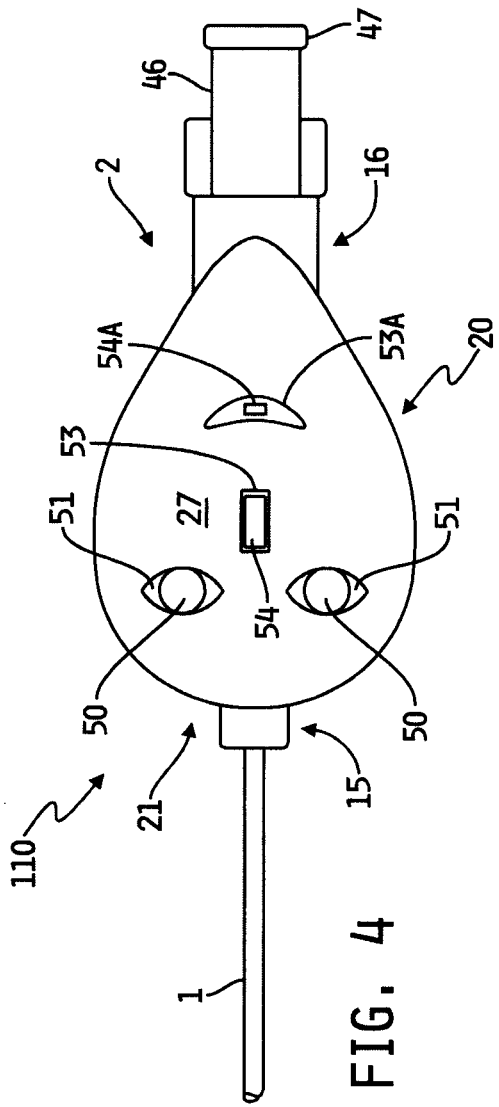
FIG. 4 is a top plan view of another illustrative needle.

For the purposes of promoting an understanding of the principles of the invention, reference will now be made to a number of illustrative embodiments illustrated in the drawing and specific language will be used to describe the same.

Referring to FIG. 1 an illustrative embodiment of a medical apparatus, for example a needle 100 is provided. FIG. 1 shows a longitudinal cross-sectional view of one embodiment of the body of an illustrative needle, for example an insufflation-type needle 100. Illustratively, the instrument 100 is used to puncture an anatomical organ structure such as for example and without limitation a cavity wall and providing a passageway via the puncture wound for communicating with the interior of the cavity. The illustrative needle 100 generally comprises a hollow outer needle 1 having a relatively sharpened or sharp tip 12 at its distal end 13. The illustrative outer needle 1 may also be referred to as a hollow needle, or a hollow tube, or an outer tube 1, and illustratively provides a means for puncturing body tissue. The proximate end of outer needle or tube 1 illustratively is coupled or joined together with a handle 2. The handle has a distal end 15 and an operative end 16. The insufflation needle 100 illustratively further comprises an inner needle 4, which may also be referred to as an inner cannula, an inner tube, or a stylet and which illustratively has at its distal end 43 a tip 42 that is blunt relative to the sharpened tip 12. Illustratively, the inner needle 4 has a smaller diameter than the hollow outer needle 1. Thus, the inner needle 4 illustratively can be received within and extend through the outer hollow needle 1. The tubes 1, 4 are generally elongated. The inner needle 4 illustratively is normally biased by a bias means 7, for example spring 7, disposed in the handle to a normal, extended, expressed, safe, or first position which extends past or beyond the sharp tip 12 of the outer needle 1. For example, the inner needle illustratively is spring-biased at the proximal end 72 of bias means 7, or spring 7, against a visual indication system or indicator, such as for example and without limitation viewing tube 8. The visual position indication system illustratively indicates the position of the inner tube, needle or stylet 4 relative to the sharp tip 12 of the outer needle 1. The other, distal, or opposing end 74 of spring 7 illustratively is placed against cone shaped end 62 of positive indicator 6. In the alternative, the bias member 7 is disposed in the handle 2, sandwiched between a mounting 63 in the operative end of the handle and the proximal end of the inner tube 62. Positive indicator 6 illustratively slides over inner needle 4 to abut negative indicator 5, as will be later explained herein. Illustratively, viewing tube 8 fits with flanges 82 against walls 22 of handle 2. Walls 29 illustratively may flare out in any desired shape, for example the oblong ovate shape of FIG. 3, in order to provide leverage to a user, for example a physician, when inserting the needle 100 into a body cavity. Those skilled in the art will also appreciate that the handle 2 could be relatively linear from end to end, but may include a separate manipulation portion 20 formed therewith or attached together therewith to provide such leverage. In addition, the manipulation portion 20 may include alternate position indication system or systems in addition to or in lieu of viewing tube or viewing window 8 or some other visual indication system as desired and as will be explained.

Referring to FIG. 2 and FIG. 3, the mechanical, dual visual position indication system comprises an integral indicator having a first or positive indicator 6 and a second or negative indicator 5 coupled to the inner tube 4. For example, a spring clip or position indicating member having a planar portion or a planar array composed of the first indicator 6 at its upper or proximal end and the second indicator 5 at its lower or distal end. The spring clip and the inner tube are coupled together and move in unison within the chamber 24 such that only one of the first and second indicators can be visible, sensible or perceptible at a time through the viewing window 86.

Handle 2 illustratively has a hollow interior cavity or bore 24 extending for a portion of the length of handle 2 containing narrow walls 26, in a generally cylindrical fashion. Outer needle 1 illustratively is anchored to handle 2 within the bore 24 at walls 26. Also, inner needle 4 is hollow, for insufflation through end 43 and from sufflation holes or aperture(s) 48.

When assembled, the blunt tip 42 of inner needle 4 is caused by the force of the spring 7 to extend past the sharpened tip 12 or distal end 13 of the hollow outer needle 1. Illustratively, in operation, when a user, for example a physician proceeds to insert the insufflation needle or instrument 100 into the body by applying pressure against the handle 2 or manipulation portion 20, opposite pressure, or resistance of the cavity wall to passage of the distal ends 13, 43, is exerted first against the blunt tip 42 of the inner needle 4 when it contacts body tissue thereby causing needle 4 to retract against the normal extending bias force of the spring 7 and into the handle 2 of instrument 100. Upon retraction, blunt tip 42 of stylet 4 will no longer extend beyond sharpened tip 12 and the body tissue or wall will instead contact the sharpened tip 12 of the outer needle 1. As the user continues to apply inserting pressure, the sharpened tip 12 will eventually pierce the body tissue or body wall. At such time as the bias force of the spring 7 is greater than the generally opposing tissue force, the spring 7 again biases, pushes or extends the blunt inner needle 4 outwardly from the handle until it is caused to extend beyond or past the sharpened tip 12 of the outer needle 1. Thus, without compressional forces applied at distal end 42 of inner needle 4, the spring 7 normally biases inner needle 4 toward a first or extended position generally outwardly away from the handle 2. Those skilled in the art will understand that this operation allows the blunt inner needle 4 to protect body tissue, for example and without limitation the internal abdominal cavity, from damage by the sharpened outer needle 1. In other words, the inner needle 4 moves between its first, expressed, safe, protective, or extended position, which is maintained through the normal extending bias force of the spring 7 in order to prevent the outer tube or needle 1 from puncturing body tissue, and a second, retracted, or unsafe position in which the bias means or spring 7 is compressed and in which sharpened tip 12 of needle 1 is exposed in order to allow needle 1 to puncture body tissue.

Also, there are provided visual means for indication that the blunt inner needle 4 is being forced outwardly away from the handle 2, such that the blunt tip 42 of inner needle 4 extends outwardly beyond the sharpened end 12 of the hollow outer needle 1. This is accomplished by the previously described mechanical position indicator systems 5, 6 (FIGS. 1-3) attached or coupled to the blunt inner needle 4, near the spring 7, which exerts a normally extending force on the blunt inner needle 4. This viewing tube 8 is hollow and illustratively is made of opaque plastic and held within the widened walls 28 of the bore 24 contained in handle 2. The viewing tube 8 illustratively has a clear or transparent window 86 located toward its distal end, which serves to indicate whether the inner needle 4 is exposed past the length of the outer needle 1 as described herein.

The visual indication means illustratively is an integral dual-indicator 5, 6, for example and without limitation a dual-color bobbin or a dual color planar array, which is coupled together with the inner needle 4. Illustratively, the lower portion 5 of the indicator is colored in a negative fashion, such as for example and without limitation red. Illustratively, the upper portion 6, is colored in a positive manner, such as green, for "go" or for "gas." Illustratively, the desired colors could be chosen from any desired color in the color spectrum as further described herein. In this way, when the inner needle 4 is in its normal, first, safe or protective position, it is fully extended past the sharpened end 12 of the outer needle 1. Only the first, illustratively green, or positive indicator 6 is exposed to or aligned with the window 86 so that it can be perceived, sensed or seen by a user. Negative indicator 5 is obscured and not perceptible or sensible when the blunt inner needle 4 extends past or beyond the sharpened end 12. However, when the blunt needle 4 is retracted, for example by resistance or a force applied to the blunt tip 42 of inner needle 4 by for example body tissue, the lower, illustratively red, negative indicator 5 is exposed to or aligned with viewing window 86 so that the observer or user perceives, senses or sees the negative indicator in the viewing window 86, while positive indicator 6 is obscured by opaque viewing tube 8 or opaque portions of the handle 2, cover or manipulation portion 20. In this fashion, the viewer knows that the sharpened outer needle end 12 is exposed, and that there is a likelihood of harm to the patient if the inner needle 4 does not return to its initial, normal or safe position. In addition, the viewing window may comprise a magnifying lens or window 86 to allow a user to better view the positive or negative indicator.

Figure 5:
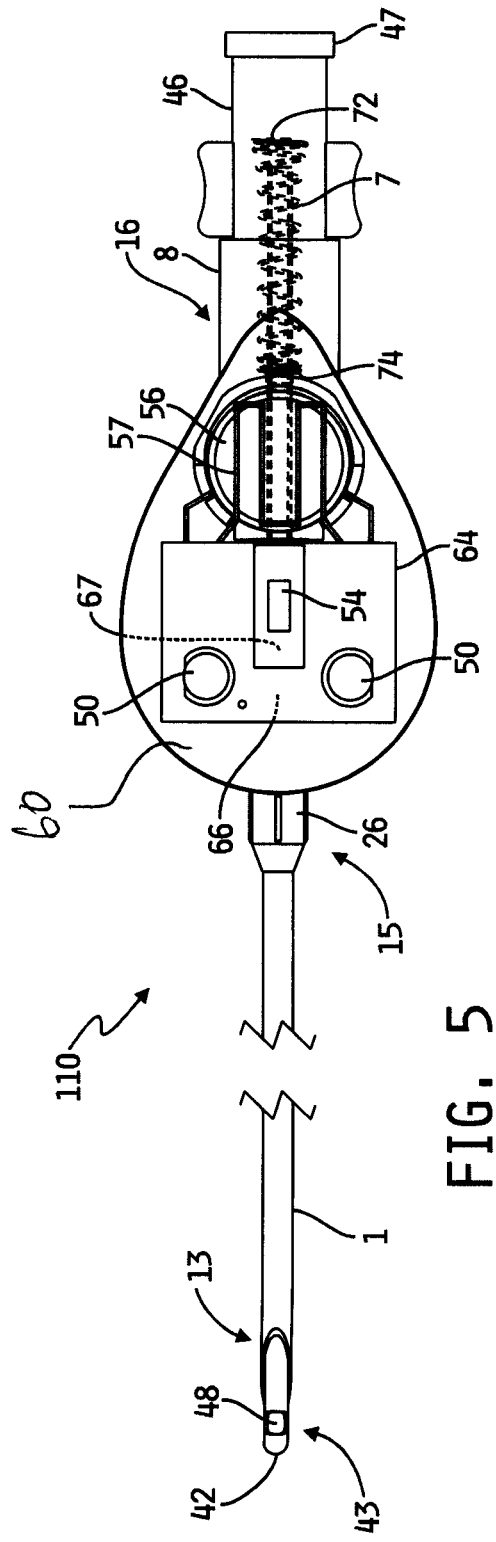
FIG. 5 is a top plan view of the illustrative needle of FIG. 4 with the cover broken away.

Medical apparatus or instrument 110 (FIGS. 4-7, 10 and 12) is substantially similar to medical apparatus or instrument 100 in construction and operation. Accordingly, like numbers are used to indicate like parts and the description of same will not be repeated. In illustrative embodiment 110, one or more electrical or electronic position indication systems are provided to the user. For example and without limitation, the user is presented with an electronic positive indication when the blunt end 42 is in the first position extended fully beyond the sharpened outer tip 12, and is presented with an electronic negative indication when the blunt end 42 is in the second position retracted within the tube such that the sharpened tip 12 extends beyond the retracted blunt end 42. For example, a light emitting diode (also referred to herein as LED) 50 may emit or display a first color and a second color. Illustratively, the first color may be a green light as a positive indication and the second color may be a red light as a negative indication. In addition, there may be a plurality of dual indicator LED(s) 50 (e.g., FIGS. 4 and 5) to provide the positive and negative indications. Each LED(s) may provide both the positive and the negative indication. For example and without limitation, referring to FIGS. 4 and 5, two separate LED(s) may both emit green light as the positive indication and the same two LED(s)s may both emit a red light as the negative indication. It will be appreciated that a single LED 50 (e.g., FIG. 7) may also be used to provide both the positive and the negative indications. For example, a single LED may emit a green light as the positive indication and the same single LED may emit a red light as the negative indication. In any event, whether multiple or single LEDs 50 are used, any single or any plurality of LEDs 50 illustratively serve(s) as a dual indicator by indicating or providing both the positive and the negative indications. The actual color of the first and second, or positive and negative, indicators or indication lights could be selectable and customizable beyond red and green. Illustratively, the desired colors could be chosen from any color in the visible light spectrum, color palette, color wheel, or color space chromaticity diagram. For example and without limitation any shades of red, orange yellow, green, blue, brown, black, indigo, violet, white, cyan, and magenta may be used. It will be appreciated that colors in the non-visible range could also be used. For example, if the user were using a viewing device operating in the infrared or ultraviolet spectrum, then the first and second colors could be chosen in that spectrum.

Instrument or medical apparatus 110 further comprises a manipulation portion 20 housing the electrical or electronic position indication system. The manipulation portion 20 or cover includes a top face 27, a distal end 21 and a proximal or operative end 23. The manipulation portion 20 illustratively is mated or coupled together with base 60 to define a cavity insulated from fluid communication with chamber 24. The electronic or electrical indication system illustratively comprises a circuit board 64, a power source 56, an energizing switch 54, 54*a*, and one or more LED(s) 50. Illustratively the power source 56 comprises a battery 56, although it could also take the form of any other suitable AC or DC power source. For example, the power source could be a power chord (not shown) that may be plugged into an electrical socket. The circuit board includes a slide contact 68, a positive indication or indicator contact 66, and a negative indication or indicator contact 67. The illustrative battery 56 is housed between contacts 57.

In operation of instrument 110, illustratively, movement of the power switch 54, 54*a* within switch aperture 53, 53*a* from a first, "off," or unenergized position, to a second, "on," or energized position, closes a circuit which illuminates the diode(s) 50, which are disposed within the diode(s) aperture (s) 51. Thus, switch 54, 54*a* is an on/off switch which could be disposed in either aperture 53 or aperture 53*a*, or both 53, 53*a* as desired. In any event, if only one switch is disposed in only one of the apertures 53, 53*a*, then the aperture without a switch could still be formed in the handle 20 if desired. So long as the inner needle is in the first, safe or extended position, a slide switch 77 coupled with the inner needle or cannula 4 via for example and without limitation a spring clip or position indicating member 76, is in contact with the positive indication contact 66 causing the diode(s) illustratively to emit a signal, for example a green light to indicate the blunt tip 42 is extended beyond the sharpened tip 12. If the inner needle 4 is in the second, unsafe or retracted position, the slide switch 77 will move rearwardly away from the sharpened tip 12 thereby breaking contact with the positive indication contact 66 and making contact with the negative indication contact 67 causing the diode(s) illustratively to emit a red light to indicate the sharpened tip 12 extends beyond the retracted blunt tip 42.

Figure 11:
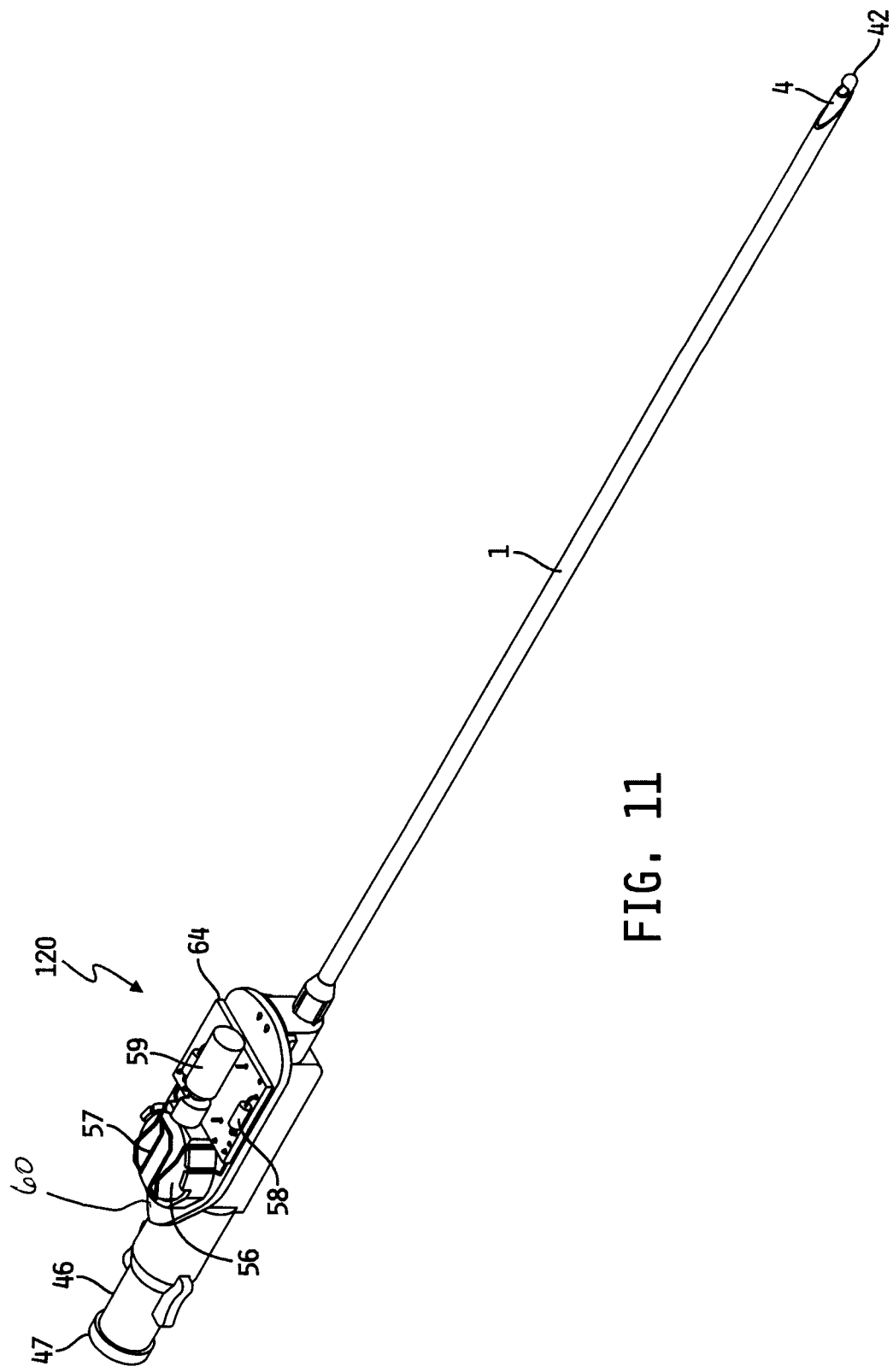
FIG. 11 is a perspective view of another illustrative needle with the cover broken away.
Figure 12:
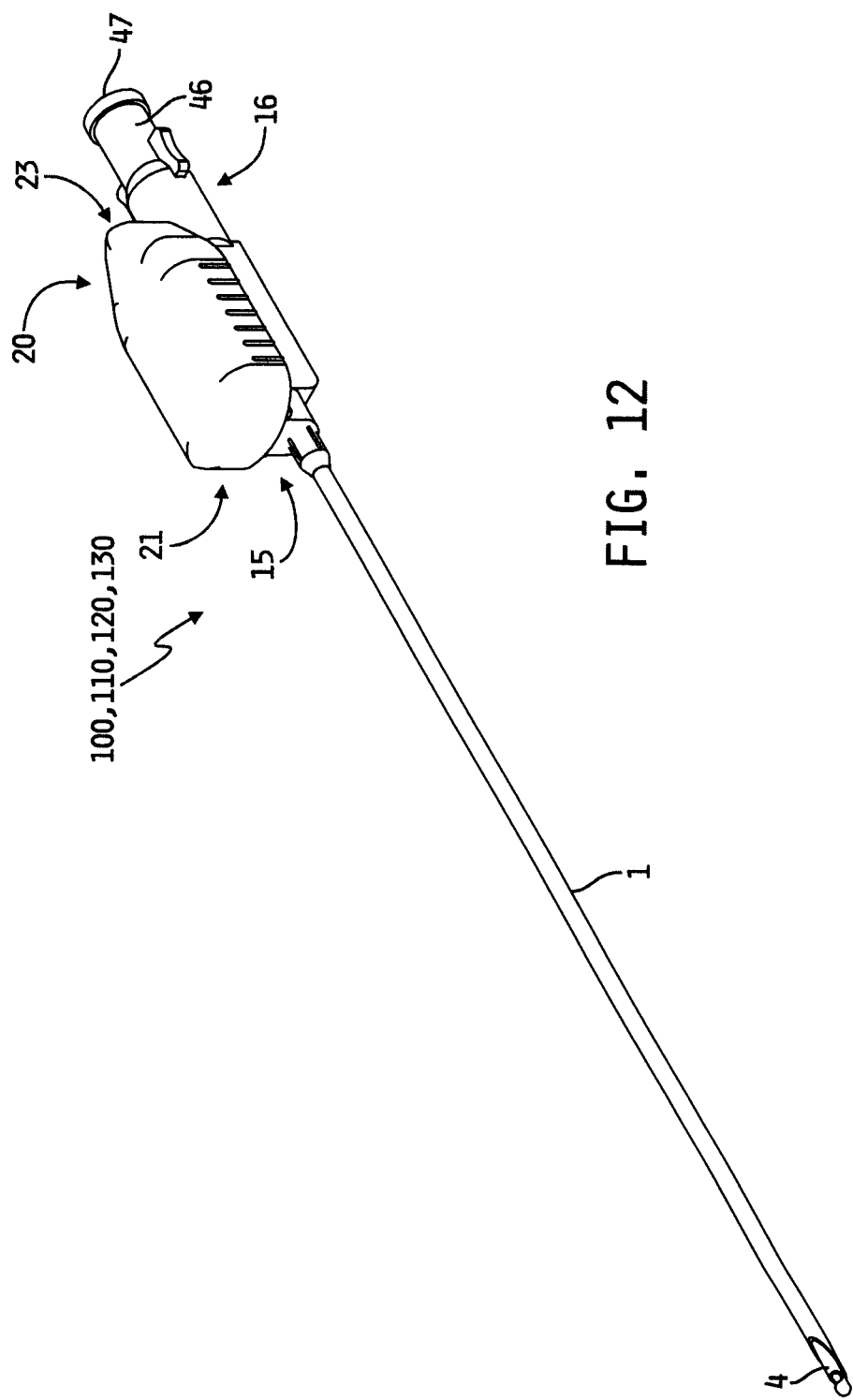
FIG. 12 is a perspective view of an illustrative needle according to the illustrative embodiments.
Figure 13:
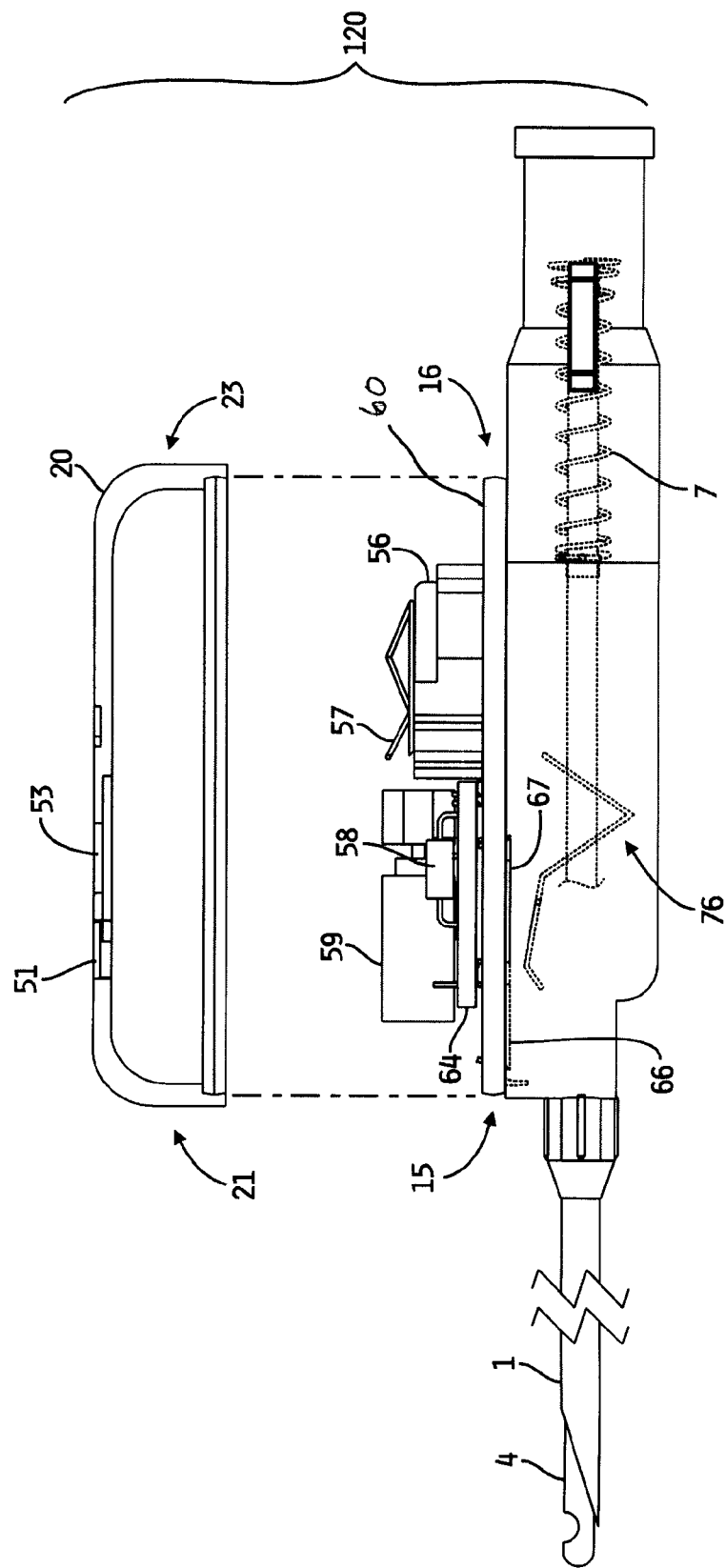
FIG. 13 is a partial exploded view of a side elevation of the illustrative needle of FIG. 11.

Another electronic indication system illustratively takes the form of tactile indication system 120 such as for example an indication system to vibrate the needle to give a positive indication, or vice versa (vibration as a negative indication) as desired (FIGS. 11, 13). Such a vibration system will work as just described for the LED indication system. Illustratively, the vibration position indication or generation system illustratively causes the apparatus to vibrate when the inner needle is in the unsafe position, and to cease vibrating when the inner needle is in the safe position. If desired, however, the vibration generation system could be configured to cause the apparatus to vibrate when the inner needle is in the safe position, and to cease vibrating when the inner needle is in the unsafe position. Similar to the LED system, the vibration generation system could comprise a power supply 56 and contact(s) 76 that move in unison with the inner needle 4 in order to alternately complete or open an electronic circuit to enable or disable vibration as desired. An illustrative tactile indication system is further described herein below.

It will be appreciated that any combination of the above and/or below described mechanical visual position indication system (red and green bobbin for example), the electronic or electrical visual position indication system (dual color LED (s) for example), the tactile position indication system (vibration for example), the aural or audible indication system 120 (warning tone or message for example) may be provided in a device 100, 110, 120, 130. For the visual indicators, optionally, there is a magnifying window or magnifying lens to enhance the color indicators as they pass through the focal point of the lens.

Illustratively, the insufflation needle 100, 110 further comprises means for introducing a fluid, such as a gas into needle 100. For example, the proximate or manipulation end 20 of the instrument 100, 110 may include a conventional luer connector, which may be connected to a fluid extension or supply tube 46. Within supply tube 46, also known as an extension tube, or otherwise connected to the extension tube 46 may be a two-way stop-cock or valve (not shown). The fluid or gas extension tube 46 may include a ridge, flange, shoulder, or waist 47, which may facilitate connection with for example a threaded stop-cock or valve. When the valve is in its open position, gas or fluid is allowed to pass through the handle and the interior of inner needle or tube 4. Aperture, sufflation hole or exit port 48 formed in the distal end 43 of needle or tube 4 provides a means for allowing fluid to flow outward from needle 4. With the stopcock in the closed position, the internal abdominal pressure, for example, is sealed, so that pneumoperitoneum is maintained. In use, the Veress needle 100, 110, is inserted into the patient's body and the surgical site is insufflated via the Veress needle by attaching a source of fluid, such as a gas, to the luer connector.

Illustratively, manipulation portion 20 may have a longitudinal length of between about 1.0 and about 2.0 inches, preferably about 1.432 inches. It may also have a transverse width of between about 0.500 and about 1.50 inches, preferably about 0.940 inches. It may have a top face 27 and side wall thicknesses of about 0.030 and about 1.00 inches, preferably about 0.060 inches, the side walls extending downwardly away from the top face between about 0.090 and about 0.250 inches, preferably about 0.190 inches. Illustratively, in FIGS. 4 and 5, diodes 50 are spaced apart, generally at their centers, about 0.200 to about 1.00 inches, preferably about 0.400 inches. The diode apertures 51 illustratively are formed as an ellipse having a transverse diameter of between about 0.125 and about 0.375 inches, preferably about 0.250 inches and a conjugate diameter of between about 0.060 and about 0.200 inches, preferably about 0.125 inches. Handle 2, illustratively has a longitudinal length of about 0.500 and about 2.00 inches, preferably about 1.50 inches.

Illustratively, the handle 2, or portions thereof such as for example the viewing window 86, may be fashioned out of clear or transparent poly-carbonate while the needles 1, 7 may be made of suitable metal, for example stainless steel. For example, portions of the handle or manipulation portion may be opaque while the viewing window is clear. It will be appreciated, however, that the device 100 may be made from any metallic, non-metallic, or composite materials or any combinations thereof using any method of manufacture appropriate to the materials used including without limitation injection molding. For example, the tube(s) could be made in whole or in part from titanium, platinum, silver, gold, brass, bronze, aluminum, lead, copper, chrome, vanadium, martensite chrome steel, steel, stainless steel, plastic, kevlar, polycarbonate, and the like or any combination thereof. Similarly, parts may be connected using any appropriate means known to those skilled in the art. The switch 54, 54A illustratively may be of the single pole, double throw type. In addition, the wiring and other components may be of any suitable construction, for example and without limitation, gold plating and/or copper or silver wiring may be used.

Figure 8:
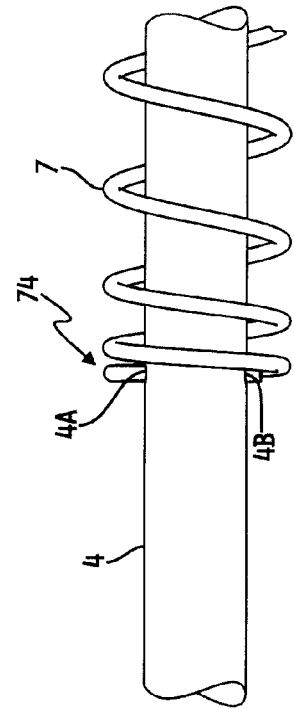
FIG. 8 is an enlarged detailed view of a portion of any of the illustrative needles.
Figure 9:
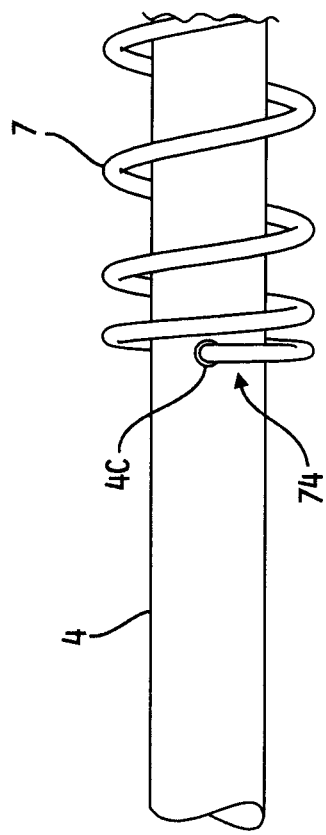
FIG. 9 is an enlarged detailed view of a portion of any of the illustrative needles.

Referring now to FIGS. 8 and 9, the unique way that spring or bias member 7 is coupled or attached together with inner needle, tube, cannula or stylet 4 can be seen. More specifically, the spring 7 and the inner tube 4 illustratively are coupled together in the proximity of opposing end 72 by the spring 7 extending inwardly through aperture 4A in hollow stylet 4, through the hollow center of the stylet 4 and outwardly through aperture 4B. The apertures 4A, 4B illustratively are holes formed through the inner needle, tube, cannula or stylet 4. The spring 7 may alternately extend inwardly through aperture 4B and outwardly through aperture 4A. Additional apertures may be used as desired. So too, it will be recognized that a single aperture 4C, with the spring 7 extending into but not extending out from the stylet 4, may be sufficient to couple together the spring 7 and the inner tube 4. It will be appreciated that this novel coupling together of the spring 7 and the inner tube 4 is applicable across all of the illustrative embodiments 100, 110, 120, 130 (see, e.g., FIGS. 6, 10, 13 and 14). This unique joining together of the spring 7 and the inner tube 4 avoids the need to use extra mounting structure and the need to use gluing, tacking, welding, press fitting or the like.

Figure 6:
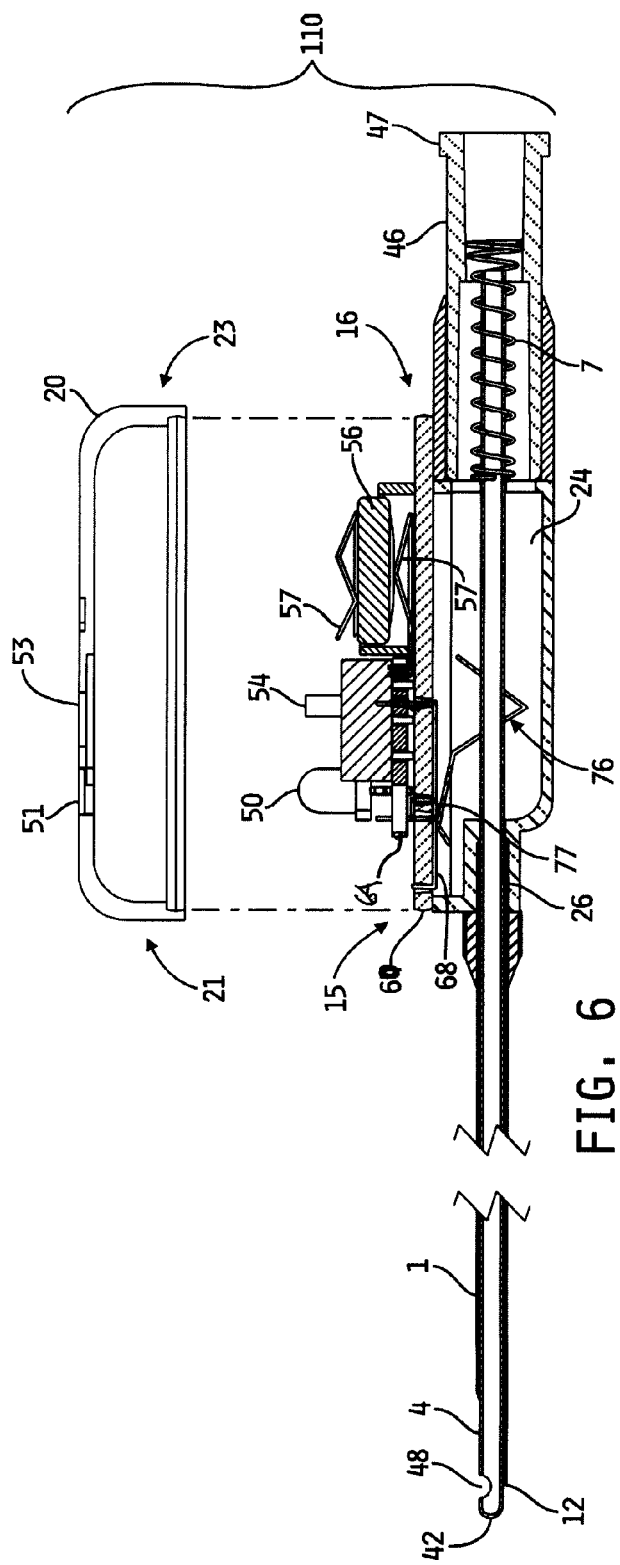
FIG. 6 is a partial exploded cross-sectional view of a side elevation of the illustrative needle of FIG. 5.
Figure 7:
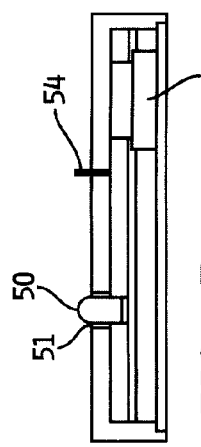
FIG. 7 is an enlarged partial cross-sectional view of a portion of the illustrative needle of FIG. 5.
Figure 10:
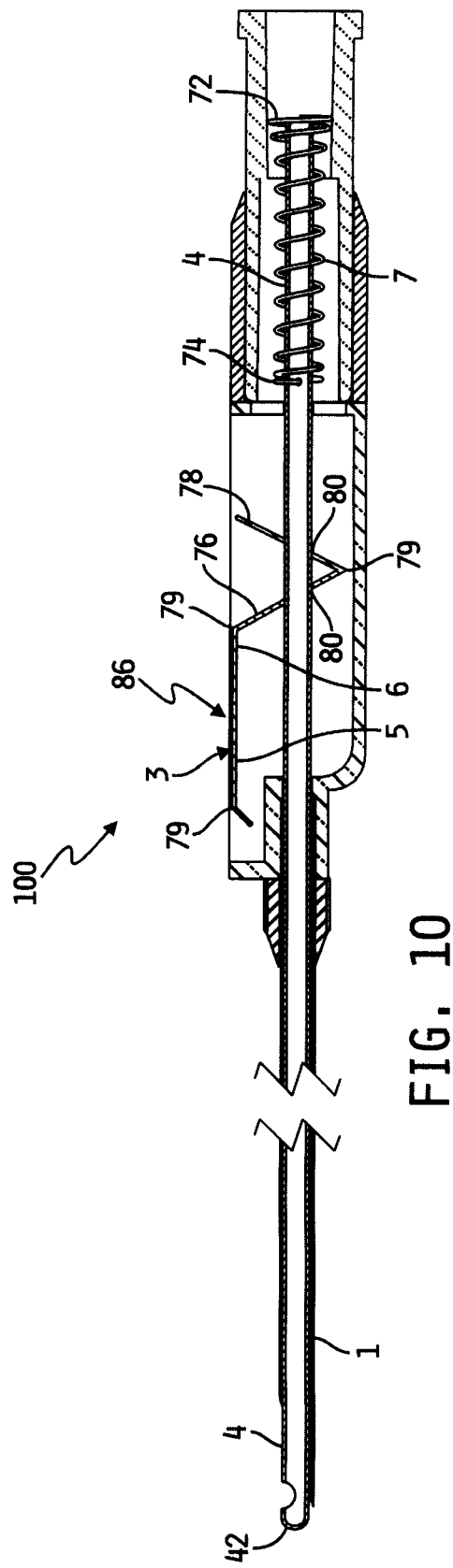
FIG. 10 is a cross-sectional view of a side elevation of another illustrative needle.

Referring for example to FIGS. 6, 10, 13 and 14, the unique way that the spring clip or position indicating member 76 and inner tube, needle, cannula or stylet 4 are coupled together can be seen. Illustratively, the position indicating member or spring clip 76 that can be formed or bent into any suitable configuration including for example a generally "S" or "Z" shape depending on which way the clip 76 is viewed or oriented in the device 100, 110, 120, 130. Illustratively, the spring may have one bend, as in a generally "V" shape (not shown), two bends 79 (FIG. 14), three bends 79 (FIGS. 6, 10, 13), or more (not shown) as desired. The orientation or number of bends are not important so long as one end of the spring provides or enables the positive and negative indications. Illustratively, at least one bend 79 defines apertures on each side of that bend such that the inner tube 4 can extend through each of the apertures in order to mount or carry the spring clip 76 on the inner tube 4. Illustratively, then the mounting bend 79 extends below the inner tube 4 and the apertures and the opposing portions of the spring clip 76 that extend generally upwardly and divergently away from the mounting bend 79 extend upwardly away from the inner tube 4 and the respective apertures. When mounted together as described, the spring clip or position indicating member 76 and inner tube 4 move together, without any need for welding, gluing, tacking, press fitting or the like, for example as the bias member or spring 7 is compressed or expanded. So, illustratively, a single bend 79 is sufficient to mount together the inner tube 4 and the clip 76. For example, in the illustrative electronic embodiments 110, 120, 130, the slide contact portion 77 of the clip 76 contacts the slide contact 68 that illustratively is embedded in base 60 as best seen in FIG. 6. The base 60 illustratively supports the components of the indication systems of embodiments 110, 120, 130, and couples with cover 20 to provide a sealed cavity separate from and sealed from fluid communication with chamber or bore 24 so that the gas does not escape from chamber 24. The switch 54, 54A moves between an "on" or energized position that enables the electronic systems and an "off" or unenergized position that disables them. As the clip 76 translates back and forth along the slide contact 77, its contact portion 77 will contact either the positive indicator contact 66 or the negative indicator contact 67. For example, in illustrative embodiment 110, when the switch 54, 54A is in the "on" position, with the inner tube 4 in its normal or extended steady-state position where it is extended or urged outwardly beyond the sharpened tip 12 by the spring 7, the contact portion 77 is in contact with the positive indicator contact 66 and the diode(s) 50 illuminate to give a positive indication, illustratively green light(s). When pressure or resistance is applied to the blunt tip 42 such that it acts against the bias force of the spring 7 in order to urge the inner tube 4 to translate inwardly into the outer tube 1 in order to expose the sharpened tip 12, the spring clip 76 concurrently and in unison with the inner tube 4 translates to move the contact portion 77 out of contact with the positive indicator contact 66 and into contact with the negative indicator contact 67 illustratively to display the diode's 50 other color, illustratively red, to indicate that the sharpened tip is exposed. It will be appreciated, then, that while three bends 79 are shown in clip 76, a single-bend configuration will allow contact with the contact slide 68 and the positive 66 and negative 67 indicator contacts. Such is the case for the other illustrative electronic embodiments 120 and 130. The non-electronic or mechanical embodiment 100, as best seen in FIG. 10, illustratively comprises two bends 79 and has a generally elongated indicator portion or assembly 3. As noted above, indicator portion or assembly 3, may comprise two different indicators, for example, two different symbols or colors, to provide a positive indicator and a negative indicator. Illustratively, indicator assembly 3 may have one portion that is painted green and shows through viewing window 86 when the inner tube 4 is in its steady-state position with the blunt end 42 extending beyond the sharpened tip 12, and have another portion painted red that is proximate to the green portion and that appears in the viewing window 86 when pressure is applied to the blunt end 42 to translate the inner tube 4 and spring clip 76 inwardly into the hollow outer tube 1. Rather than being painted, colored tape could be applied to the spring clip. So, too, dye or a radioactive or phosphorescent coating and the like could be used. The viewing window 86, as noted, may comprise a magnifying glass.

Illustrative Medical apparatus or instrument 120 (FIGS. 11-13), which also is described above, is substantially similar to medical apparatus or instruments 100 and 110 in construction and operation. Accordingly, like numbers are used to indicate like parts and the description of same will not be repeated. Illustrative embodiment 120 provides a different method of providing a positive indication, representing the steady-state, safe or normal position or configuration wherein the blunt end 42 extends beyond the sharpened tip 12, and a negative or unsafe indication wherein the sharpened tip 12 extends beyond the blunt end 42. Illustratively, indicator 59 may be an audible or aural signal indicator such as for example an audio transducer or a sound chip, or a tactile signal indicator such as for example a vibration motor, or it may be a combination of an aural and a tactile signal indicator. The indicator 59 illustratively is mounted on circuit board 64, as is integrated circuitry 58, which in turn are mounted on or coupled with base 60. Illustratively, the audio transducer could have a first, safe or positive indicator wherein it is silent during the normal or safe position and could emit a second indicator for example an aural signal or warning when the sharpened tip 12 extends beyond the blunt end 42 or vice versa. Alternately, the audio transducer 59 could emit a first or positive indicator comprising an aural or audibly perceptible warning whenever the steady-state or normal or safe position is extant and a second or negative indicator comprising an aural or audibly perceptible warning distinguishable from the first aural or audible warning whenever the sharpened tip 12 extends beyond the blunt end 42. Similarly, as described above, the vibration motor could be disabled during the normal position and could be enabled to cause the apparatus 120 to vibrate when the sharpened tip 12 extends beyond the blunt end 42 or vice versa. Alternately, the vibration motor 59 could emit a first, safe or positive indicator perceptible as a tactile signal or warning whenever the normal, steady-state or safe position is extant and a second, negative or unsafe indicator perceptible as a tactile signal or warning that is distinguishable from the first tactile signal or warning whenever the sharpened tip extends beyond the blunt end 42. It will be appreciated that indicator 59 could provide both a perceptible tactile and/or an aural warning. For example, the device 120 could vibrate whenever the inner tube 4 is in the steady-state or extended position and an aural warning could sound whenever the inner tube 4 retracts or is urged into the outer tube 1 to expose the sharpened tip or vice versa. So, too, both a positive indication aural and tactile warning could be emitted when the inner tube 4 is in the steady-state, normal or extended position, and a negative indication aural and tactile warning distinguishable from the positive indication warnings could be emitted whenever the sharpened tip 12 is exposed. It will be appreciated that any combination or permutation of aural and tactile warnings also fall within the scope of the invention. The positive and negative indicators or indications of whichever indicator 59 (tactile or aural) or combination of indicators (tactile and aural) is used are triggered by the contact portion 77 contacting the respective positive indicator contact lead 66 or negative indicator contact lead 67 as described above with illustrative embodiment 110.

Figure 14:
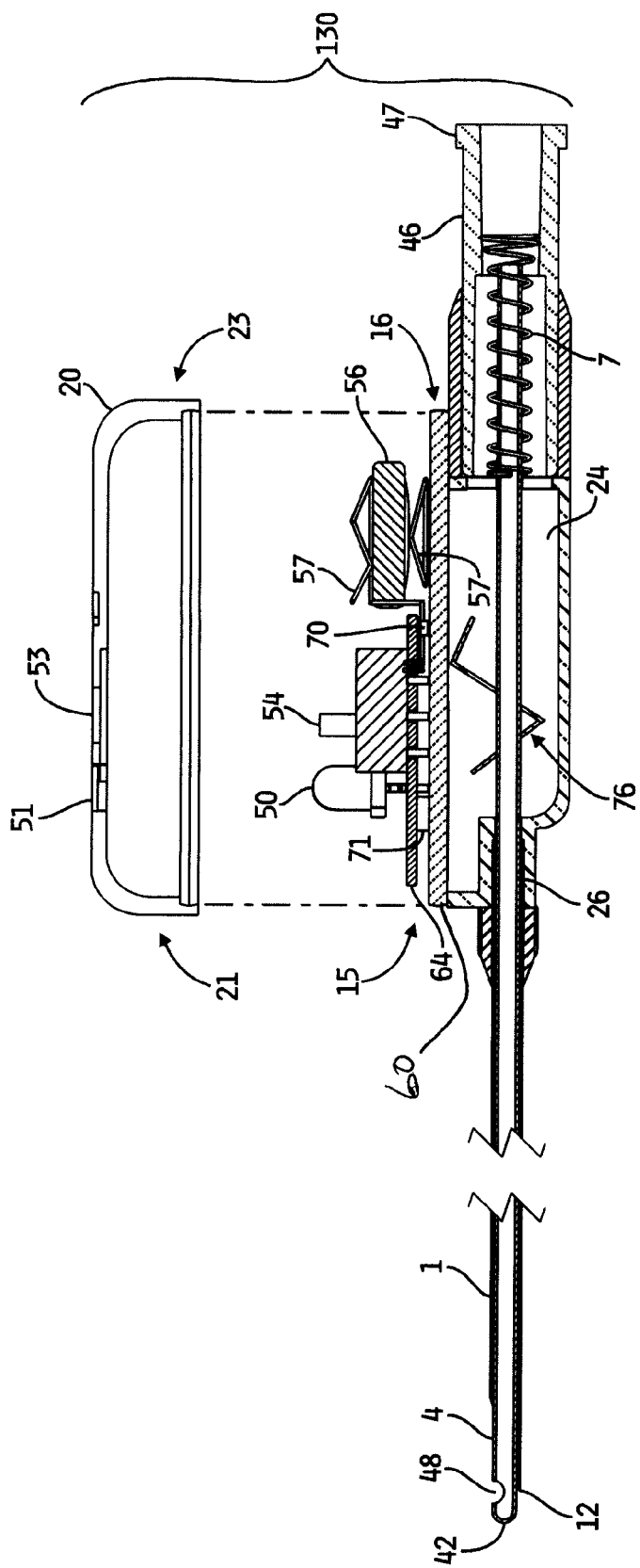
FIG. 14 is a partial exploded cross-sectional view of a side elevation of another illustrative needle.

Referring to FIG. 14, another illustrative embodiment is disclosed and comprises a transmitter 70 and a receiver 71. Illustratively, when the switch 54 is turned on, the transmitter 70 emits a signal that is detectable or not by the receiver 71 depending on the position of the spring clip or position indicating member 76. For example, whenever the inner tube 4 is in the normal, safe, steady-state or extended position, the clip 76 illustratively covers the transmitter 70 so that the receiver does not receive a signal and the diode(s) 50 (or indicator 59) provide the positive indicator or indication signal or warning, for example a green light (or first audible signal or first vibration). Whenever the inner tube is retracted within the outer tube 1 such that the sharpened tip 12 is exposed, the clip 76 illustratively uncovers the transmitter 70 so that the signal may travel within the open space within the sealed cavity or chamber defined between the cover 20 and the base 60 to the receiver 71 causing the circuitry to exhibit the negative indicator signal or warning, for example a red light (or second audible signal or second vibration). In the alternative, the positive indicator or indication signal could be exhibited when the transmitter is uncovered, with the negative indicator or indication signal being exhibited when the transmitter is covered. In addition, the positive and negative indication or indicator signals or warnings could be determined by the clip 76 covering and uncovering the receiver. So too, the positive and negative indication or indicator warnings or signals could be determined by a slide contact arrangement as described in conjunction with illustrative embodiments 110 and 120. For example, when the contact portion 77 contacted the indicator contact lead 66 or positive contact 66, the transmitter 70 could be enabled and a signal emitted for sensing by the receiver 71. In the alternative, when the contact portion 77 contacted the negative contact 67 or negative contact lead 67, the transmitter 70 could be enabled and a signal emitted for detecting or sensing by the receiver. Alternatively, the spring clip or position indicating member 76 could determine or control when the receiver 71 was enabled or disabled. Again, any combination or permutation of the operation of the receiver and transmitter fall within the scope of the invention, as do the type of signal or warning (visual, aural, tactile, radio frequency, odiferous, or combinations thereof) that are triggered. The signal itself may be any suitable signal including for example and without limitation an infra red signal, a visible signal (for example a light including for example and without limitation a laser beam), a smell or odor, an aural signal and/or a radio frequency or other electro-magnetic signal.

As noted, any combination or permutation of the above described indicators and indications, as well as the way they are enabled or triggered, fall within the scope of the invention. For example, and without limitation, one illustrative embodiment could operate as follows: As the needle is enabled by activating the switch 54 to the "on" position, the diode(s) 50 emit a first color, for example green, as a positive indication or indicator that the needle is in the normal or steady-state configuration wherein the blunt tip 42 is in the extended position such that it extends outwardly beyond the sharpened tip 12 and the first or indicator contact lead 66 and the contact portion 77 or in contact with one another. As the blunt tip 42 is pressed against an object that offers resistance, such as the flesh of a patient, the blunt tip 42 translates from the normal extended position and into the inner tube 1 against the bias force of the spring 7 thereby exposing the sharpened tip 12 and placing the contact slide portion 77 and the negative indication or indicator contact 67 into contact with one another thereby causing the diode(s) 50 to turn or emit a second signal or color, for example red, and/or another signal such as causing the vibration motor 59 illustratively to begin vibrating, to provide a second or negative indicator(s) or indication(s) that the sharpened tip 12 is exposed. In addition to, or in lieu of the vibration, the transducer 59 could sound a warning tone, for example a warbling tone, or emit a warning message such as for example "caution." When the needle is fully inserted, thereby overcoming the resistance on the blunt tip 42 from the object such as the patient's flesh, the spring bias 7 urges the blunt tip 42 back to its extended, safe or normal position extending beyond the sharpened tip 12, which illustratively allows the contact slide portion 77 to make contact with the positive indication or indicator contact 66 to cause the diode(s) 50 to again emit the first signal or color, for example green, or even a third color if desired, and to cause the vibration motor 59 to stop or cease vibrating or to emit a different signal or vibration, and/or to cause the transducer 59 to sound a second tone, for example a steady tone, or to emit a message such as for example "The needle has landed" or the "tube is in the safe position." Instead of, or in addition to using the positive 66 and negative 67 indicator contact leads as described, the contact slide portion 77 could mask and unmask a transmitter 70 and/or a receiver 71 that enables or triggers the above described positive and negative indicators or indications. Again, it will be appreciated that the above is illustrative, and any combination or permutation of the various signals and signal triggers would fall within the scope of the invention. For example, one embodiment could have a visual only signal using diode(s) 50, another embodiment could have a tactile only signal using vibrating motor 59, another embodiment could have an aural only signal using transducer 59, and each of the foregoing could use the electronic leads configuration, the transmitter/receiver configuration, or a combination of the two. So, too, any or all of the foregoing embodiments, could have a non-electronic or mechanical signal (e.g., FIGS. 1-3 and 10) in addition to one, or more, or all of the foregoing electronic signal configurations.

Another illustrative embodiment comprises a hollow outer tube having a proximal end and a distal end, the distal end comprising a sharpened tip; an hollow inner tube having a proximal end and a distal end, the distal end comprising a blunt tip, and the inner tube defining a hollow core extending from the inner tube's proximal end to the inner tube's distal end, the distal end including an aperture in fluid communication with the hollow core; a handle having a distal end and an operative end and defining an interior chamber; a position indicator system having a first indicator and a second indicator; a bias member having a distal end and a proximal end; wherein the proximal end of the outer tube and the distal end of the handle are connected together; wherein the hollow inner tube is slidingly disposed within the hollow outer tube and the interior chamber; wherein the distal end of the bias member extends inwardly through an aperture in the proximity of the proximal end of the hollow inner tube to couple together the hollow inner tube and the bias member; wherein the position indicator system includes an indicating assembly (for example an indicating window or a transducer, or a vibrator, or LEDs, or an IR receiver, etc.) and a position indicating (for example a spring clip) carried by the hollow inner tube; wherein the position indicating member includes a bend having a first aperture on one side of the bend and a second aperture on another side of the bend, the first and second apertures being opposed to and in alignment with one another and wherein the hollow inner tube extends through the first and second opposed apertures on either side of the bend; wherein the position indicating member is disposed within the chamber and operatively associated with the position indicating member; wherein the bias member normally urges the hollow inner tube outwardly away from the operative end to a first position wherein the blunt tip extends beyond the sharpened tip thereby moving the position indicating member into operative alignment with a portion of the indicating assembly that enables the first indicator alone; and wherein when a force sufficient to overcome the normal force of the bias member is applied to the blunt end the hollow inner tube, the hollow inner tube moves to a second retracted position wherein the blunt tip no longer extends beyond the sharpened tip thereby removing the position indicating member out of operative alignment with the portion of the indicating assembly that enables the first indicator alone and into operative alignment with a second portion of the indicating assembly that enables the second indicator alone.

While the invention has been illustrated and described in detail in the foregoing drawings and description, the same is to be considered as illustrative and not restrictive in character, it being understood that only illustrative embodiments thereof have been shown and described and that all changes and modifications that come within the spirit of the invention are desired to be protected.

What is claimed is:

1. A medical apparatus comprising:
   a hollow outer tube having a proximal end and a distal end, the distal end comprising a sharpened tip;
   a hollow inner tube having a proximal end and a distal end, the distal end comprising a blunt tip, and the inner tube defining a hollow core extending from the inner tube's proximal end to the inner tube's distal end, the distal end including an aperture in fluid communication with the hollow core;
   a handle having a distal end and an operative end and defining an interior chamber;
   a position indicator system having a first indicator and a second indicator;
   a bias member having a distal end and a proximal end;
   wherein the proximal end of the outer tube and the distal end of the handle are connected together;
   wherein the hollow inner tube is slidingly disposed within the hollow outer tube and the interior chamber;
   wherein the distal end of the bias member extends inwardly through an aperture in the proximity of the proximal end of the hollow inner tube to couple together the hollow inner tube and the bias member;

wherein the position indicator system includes an indicating assembly integrated into the handle and a position indicating member carried by the hollow inner tube;

wherein the position indicating member includes a spring clip having a bend with a first aperture on one side of the bend and a second aperture on another side of the bend, the first and second apertures being opposed to and in alignment with one another and wherein the hollow inner tube extends through the first and second opposed apertures on either side of the bend;

wherein the position indicating member is disposed within the chamber and operatively associated with the position indicator system;

wherein the bias member normally urges the hollow inner tube outwardly away from the operative end to a first position wherein the blunt tip extends beyond the sharpened tip thereby moving the position indicating member into operative alignment with a portion of the indicating assembly that enables the first indicator alone; and wherein when a force sufficient to overcome the normal force of the bias member is applied to the blunt end the hollow inner tube, the hollow inner tube moves to a second retracted position wherein the blunt tip no longer extends beyond the sharpened tip thereby removing the position indicating member out of operative alignment with the portion of the indicating assembly that enables the first indicator alone and into operative alignment with a second portion of the indicating assembly that enables the second indicator alone.

2. The medical apparatus of claim 1 wherein the first indicator and the second indicator comprise a single integrated component.

3. The medical apparatus of claim 1 wherein the first indicator comprises a positive indicator and the second indicator comprises a negative indicator.

4. The medical apparatus of claim 1, wherein the position indicator system comprises a visible indicator system.

5. The medical apparatus of claim 1, wherein the position indicator system comprises an aural indicator system.

6. The medical apparatus of claim 1, wherein the position indicator system comprises a tactile indicator system.

7. The medical apparatus of claim 1, wherein the position indicator system comprises an infrared indicator system.

8. The medical apparatus of claim 1, wherein the position indicator system comprises a combination of a visible indicator system and a tactile indicator system.

9. The medical apparatus of claim 1, wherein the position indicator system comprises a combination of a visible indicator system and an aural indicator system.

10. The medical apparatus of claim 1, wherein the position indicator system comprises a combination of an aural indicator system and a tactile indicator system.

11. The medical apparatus of claim 1, wherein the position indicator system comprises a combination of a visible indicator system, a tactile indicator system, and an aural indicator system.

12. The medical apparatus of claim 1, wherein the position indicator system comprises a combination of a visible indicator system, a tactile indicator system, an aural indicator system, and an infrared indicator system.

13. The medical apparatus of claim 1, wherein the position indicator system comprises a mechanical indicator system.

14. The medical apparatus of claim 1, wherein the position indicator system comprises an electrical indicator system.

15. The medical apparatus of claim 1, wherein the position indicator system comprises an electro-mechanical indicator system.

16. The medical apparatus of claim 4, wherein the electronic visual indicator system comprises a light emitting diode (LED) configured to emit at least two colors.

17. The medical apparatus of claim 1 wherein the spring clip includes a slide contact portion movable to operatively contact a positive indicator contact and a negative indicator contact.

18. The medical apparatus of claim 17 further including a power source for illuminating an indicator upon movement of the spring clip slide contact portion to operatively contact the positive indicator contact and the negative indicator contact.

* * * * *